United States Patent [19]

Maas, Jr.

[11] 4,117,083

[45] Sep. 26, 1978

[54] PROCESS FOR INCREASING THE REACTION RATE OF $UO_2F_2$

[75] Inventor: Edward T. Maas, Jr., Kendall Park, N.J.

[73] Assignee: Exxon Research & Engineering Co., Linden, N.J.

[21] Appl. No.: 752,722

[22] Filed: Dec. 21, 1976

[51] Int. Cl.² ............................................. C01G 43/00
[52] U.S. Cl. .................................... 423/253; 423/258
[58] Field of Search ................. 252/301.1 R; 423/253, 423/258; 260/429.1

[56] References Cited

PUBLICATIONS

Chakravorti, M. C. et al., "Fluoro Complexes of Hexavalent Uranium-IV" *J. Inorg. Nucl. Chem.*, vol. 34, No. 9, 1972, pp. 2867–2874.
Chemical Abstracts, 76:92956m, 1972.
Chemical Abstracts, 82:132476n, 1975.
Dewan, J. C. et al., "Fluoride Crystal Structures," *J. Chem. Soc., Dalton*, 1975, Issue 21, pp. 2171–2174.

*Primary Examiner*—Benjamin R. Padgett
*Assistant Examiner*—Deborah L. Kyle
*Attorney, Agent, or Firm*—Ronald D. Hantman; Jerome E. Luecke

[57] ABSTRACT

A process for increasing the average reaction rate of reduction of $UO_2F_2$. The $UO_2F_2$ is treated with an organic compound which interacts with the $UO_2F_2$. The combination is decomposed to yield $UO_2F_2$ in a kinetically reactive state.

48 Claims, No Drawings

PROCESS FOR INCREASING THE REACTION RATE OF UO$_2$F$_2$

BACKGROUND OF THE INVENTION

This invention relates to a process for increasing the average reaction rate of reduction of UO$_2$F$_2$.

UO$_2$F$_2$ is an important material used in the nuclear fuel cycle for nuclear power reactors. An important chemical reaction of UO$_2$F$_2$ is reduction to UO$_2$ for use as nuclear fuel. This reduction is also important in the Fluorox process which is a scheme to generate UF$_6$ for subsequent isotope enrichment without the use of elemental fluorine.

The reactions of the Fluorox process form the basis of a commercial process for the production of UF$_6$ by a method not requiring the use of fluorine, see e.g. L. M. Ferris, J. Amer. Chem. Soc. 79, 5419 (1975). The reactions which comprise the process are:

$$2UF_4 + O_2 \rightarrow UO_2F_2 + UF_6 \quad (1)$$

$$UO_2F_2 + H_2 \rightarrow UO_2 + 2HF \quad (2)$$

$$UO_2 + 4HF \rightarrow UF_4 + 2H_2O \quad (3)$$

All of these reactions must be carried out at high temperatures in order that reasonable quantities of the desired product are produced.

The utility of the Fluorox process in general is in part limited by rates of this reduction reaction. An increased rate of reaction of UO$_2$F$_2$ toward reduction would be therefore desirable.

In an attempt to increase the rate of reactions 1 and 2, solid heterogeneous catalysts have been added, see e.g. A. Ekstrom, G. E. Batley and D. A. Johnson, J. of Catalysis 34, 106 (1974); ibid. 34, 368 (1974). While this has been successful, the presence of this second solid phase would require elaborate separation procedures to free the desired product from the catalyst material in a commercial application.

Our invention includes a method to increase the rate of reaction 2 by means of a treatment of the UO$_2$F$_2$ employed.

During the thermal decomposition of a group of complexes which are defined in more detail below, an increase in the surface area of the UO$_2$F$_2$ was noted. This increased surface area of the UO$_2$F$_2$ implied that the recovered UO$_2$F$_2$ should be more reactive to subsequent chemical reactions of the solid-gas and solid-liquid types, with the solid being UO$_2$F$_2$.

However, this is only partially true. The prior art includes a French patent, French 2,045,692, filed June 20, 1969, issued Mar. 5, 1971, in which water vapor treatment of uranyl fluoride powder at 60° C in H$_2$O vapor increase surface area of UO$_2$F$_2$ from ~0.3 m$^2$/g to 23. m$^2$/g. It can be seen from our Table I that the average reaction rate of reduction decreases rather than increases when a treatment with water vapor is employed.

The present invention discloses a process for increasing the rate of reduction.

SUMMARY OF THE INVENTION

The present invention is a process for increasing the average rate of reduction of UO$_2$F$_2$ by combining UO$_2$F$_2$ with an organic compound capable of interacting with said UO$_2$F$_2$ to form a combination, the compound being one of the following: amines, aliphatic heterocyclic amines, aromatic heterocyclic amines, aliphatic amides, sulfides, aliphatic heterocyclic sulfides, sulfoxides, aliphatic heterocyclic sulfoxides, sulfones, aliphatic heterocyclic sulfones, alcohols, and mixtures thereof. These compounds are further defined below.

The resulting combination is decomposed to yield UO$_2$F$_2$ in a kinetically reactive state. The increased reactivity allows an improvement to the process for producing UF$_6$ which involves the production of UO$_2$F$_2$ and its subsequent reaction.

DESCRIPTION OF THE PREFERRED EMBODIMENT

The present invention includes a process to increase the average reaction rate of reduction of UO$_2$F$_2$. In addition, the invention includes an improvement of a process to produce UF$_6$.

UO$_2$F$_2$ is combined with an organic compound having Lewis base characteristics and capable of interacting with the UO$_2$F$_2$.

The combination is decomposed to yield UO$_2$F$_2$ in a kinetically reactive state.

Compounds of the above described type were prepared by treating solid uranyl fluoride with the organic Lewis base. The base may be either liquid or gaseous and may in each case be diluted with an inert material. For example, the liquid organic Lewis base may be diluted with benzene or acetone before it is contacted with the solid uranyl fluoride. Likewise the organic Lewis base in gaseous form may be diluted with nitrogen gas and then passed over the solid uranyl fluoride to effect reaction. The temperature of the reaction may be varied with the lower limit being, in each specific case, the solidifaction temperature of the organic Lewis base and the upper limit in each case being the temperature at which decomposition of the product compound is initiated.

The time for an equilibrium content of organic Lewis base to be included by the UO$_2$F$_2$ varies depending on the chemical activity of the base in question. That is to say, an organic base in concentrated liquid form has a higher chemical activity towards reaching an equilibrium concentration in the resulting compound than that of a gas stream consisting of, for example, only 0.5–1.0% or less of the same base in gaseous form. In general with neat liquid bases, 24–36 hrs. reaction times are necessary for complete reaction to occur at ambient temperatures (20° C). When the organic is presented in vapor form to the uranyl fluoride, longer reaction times on the order of 3–7 days are necessary depending upon the vapor pressure of the organic base and the temperature of the reaction.

An increase in the temperature at which the reaction is carried out will also cause an increase in the rate of the reaction. For example, contacting UO$_2$F$_2$ with refluxing pyridine will shorten the reaction time to about 1–2 hours.

UO$_2$F$_2$ is soluble in low molecular weight alcohols and in these cases the solid complex was isolated by evaporation of the excess organic base. Similarly, when water (or water vapor) was present in appreciable amounts together with the organic bases, mixed complexes containing both water and the organic base were formed with UO$_2$F$_2$. This was found to be the case especially in the pyridine/UO$_2$F$_2$ system.

The second step of the Fluorox process can be summarized by the following reaction:

$$UO_2F_2 + H_2 \triangle UO_2 + 2HF$$

By treating the $UO_2F_2$ destined for this step from the initial step in the overall process in the manner described in this discussion, one could effect an increase in reaction rate of the desired reduction. This would enable the reaction to be carried out at a lower temperature, or for a shorter period of time or both. For example, the $UO_2F_2$ isolated from the initial reaction of the Fluorox process could be treated with liquid pyridine in sufficient quantity to wet the entire sample. This could be done up to the boiling point of pyridine of 115° C. This would effect formation of the desired compound. The compound could be then isolated from the excess pyridine (i.e., that amount of pyridine not incorporated in the crystal lattice of the $UO_2F_2$) by such techniques as filtration or vacuum distillation. The isolated solid compound could then be directly injected into the appropriate reduction apparatus at temperatures high enough to effect the reduction (T>300° C). At this point the included pyridine would be driven from the $UO_2F_2$ and would be contained as a vapor in the off gas from the reaction vessel. Passage of the off gas through an appropriate condenser would recover the pyridine for subsequent recycle into the process.

When compounds were formed between $UO_2F_2$ and the Lewis bases, the stoichiometry could be characterized by the (moles base/MOLES $UO_2F_2$) = (B/U) ratio. These ratios were typically in the range 0.5–3.0.

Each material isolated exhibited a unique X-ray powder diffraction pattern different from solid $UO_2F_2$ and also different from those of the other compounds indicative of discrete compound formation in each case.

The organic Lewis bases that form the compositions of the present invention include generalized classes of nitrogen, sulfur and oxygen containing bases. All of these classes are defined below.

It is to be appreciated that commercial grades of the Lewis bases useful in this invention may contain water. While it is preferable that no water be present, the invention contemplates the use of such bases containing up to about 5% water.

Suitable Lewis bases for the present invention include the following listed below, and mixtures thereof:

1. Amines of generalized formula $$R_1-\underset{\underset{R_3}{|}}{N}-R_2$$

where at least one of radicals $R_1$, $R_2$ and $R_3$ is an aliphatic or an aromatic carbon network with carbon numbers of 1 to 6 with the remaining radicals, if any, being H.

2. Aliphatic heterocyclic amines of generalized formula $$\left( \underset{\underset{R_4}{|}}{\underset{N}{(-C-)_n}} \right)_{R_{n1}}^{R_{n2}}$$

where $R_4$ is H or an aliphatic radical of carbon number of 1 to 4 and $n$ can assume values of 4 to 6 inclusive and $R_{n1}$ and $R_{n2}$ are each individually H or methyl, each of $R_{n1}$ and $R_{n2}$ being the same or different.

For example, when $n = 4$, then the compound would be

[structure showing 4-membered ring with C atoms bearing $R_{11}, R_{12}, R_{21}, R_{22}, R_{31}, R_{32}, R_{41}, R_{42}$ and N bearing $R_4$]

and when $n = 6$, the compound would be

[structure showing 6-membered ring with C atoms bearing $R_{11}, R_{12}, R_{21}, R_{22}, R_{31}, R_{32}, R_{41}, R_{42}, R_{51}, R_{52}, R_{61}, R_{62}$ and N bearing $R_4$]

3. Aromatic heterocyclic amines of generalized formula $$\left( \underset{\underset{(R_5)_a}{|}}{\underset{N}{(=C-)_m}} \right)_{R_{ml}}$$

where $m$ is an integer of 4 to 6 inclusive and $a = 1$ when $m = 4$ or 6 and $a = 0$ when $m = 5$, and $R_5$ is H or aliphatic radical of carbon number 1 to 4 and $R_{ml}$ is H or methyl.

For example, when $m = 5$, the compound would be

[pyridine-type structure with C atoms bearing $R_{11}, R_{21}, R_{31}, R_{41}, R_{51}$ and N]

4. Aliphatic amides of formic acid of generalized formula $$H-\overset{\overset{O}{\|}}{C}-N\overset{R_6}{\underset{R_7}{\diagdown}}$$

where $R_6$ and $R_7$ are each individually H or an aliphatic radical of carbon number 1 to 3, each of $R_6$ and $R_7$ being the same or different.

An example of this type of compound is $$H-\overset{\overset{O}{\|}}{C}-N\overset{CH_3}{\underset{CH_3}{\diagdown}}$$

5. Alcohols of generalized formula $$R_8 - O - H$$

where $R_8$ is an aliphatic radical of carbon number 1 to 4 inclusive.

An example of this type of compound is $$H-\underset{\underset{H}{|}}{\overset{\overset{H}{|}}{C}}-\underset{\underset{H}{|}}{\overset{\overset{H}{|}}{C}}-\underset{\underset{H}{|}}{\overset{\overset{H}{|}}{C}}-OH$$

6. Sulfides of generalized formula $$R_9 - S - R_{10}$$

where $R_9$ and $R_{10}$ are the same or different aliphatic radicals having a carbon number of 1 to 3.

An example of this type of compound is $$H-\underset{\underset{H}{|}}{\overset{\overset{H}{|}}{C}}-\underset{\underset{}{|}}{\overset{\overset{H}{|}}{C}}-S-\underset{\underset{H}{|}}{\overset{\overset{H}{|}}{C}}-\underset{\underset{H}{|}}{\overset{\overset{H}{|}}{C}}-H$$

7. Aliphatic heterocyclic sulfides of generalized formula $$\left( \underset{S}{(-\overset{R_{p1}}{\underset{R_{p2}}{C}}-)_p} \right)$$

where $p$ is an interger between 4 and 6 inclusive and $R_{p1}$ and $R_{p2}$ are each individually H or methyl, each of $R_{p1}$ and $R_{p2}$ being the same or different.

An example of this type of compound is (cyclic structure with C-C-C-C-S)

8. Sulfoxides of generalized formula $$R_{11} - \underset{\underset{O}{\parallel}}{S} - R_{12}$$

where $R_{11}$ and $R_{12}$ are aliphatic radicals of carbon number 1 to 3. An example of this type of compound is $$H-\underset{\underset{H}{|}}{\overset{\overset{H}{|}}{C}}-\underset{\underset{O}{\parallel}}{S}-\underset{\underset{H}{|}}{\overset{\overset{H}{|}}{C}}-H$$

9. Aliphatic heterocyclic sulfoxides of generalized formula $$\left( \underset{\underset{\underset{O}{\parallel}}{S}}{(-\overset{R_{q1}}{\underset{R_{q2}}{C}}-)_q} \right)$$

where $q$ is an integer of 4 to 6 inclusive and $R_{q1}$ and $R_{q2}$ are each individually H or methyl, each of $R_{q1}$ and $R_{q2}$ being the same or different. An example of this type of compound is (cyclic structure with R groups and S=O)

10. Sulfones of generalized formula $$R_{13} - \underset{\underset{O}{\nearrow} \underset{O}{\nwarrow}}{S} - R_{14}$$

where $R_{13}$ and $R_{14}$ are aliphatic radicals of carbon 1 to 3

An example of this type of compound is $$H-\underset{\underset{H}{|}}{\overset{\overset{H}{|}}{C}}-\underset{\underset{H}{|}}{\overset{\overset{H}{|}}{C}}-\underset{O \nearrow \nwarrow O}{S}-\underset{\underset{H}{|}}{\overset{\overset{H}{|}}{C}}-\underset{\underset{H}{|}}{\overset{\overset{H}{|}}{C}}-H$$

11. Aliphatic heterocyclic sulfones of generalized formula $$\left( \underset{\underset{O \nearrow \nwarrow O}{S}}{(-\overset{R_{r1}}{\underset{R_{r2}}{C}}-)_r} \right)$$

where $r$ is an integer of 4 to 6 inclusive and $R_{r1}$ and $R_{r2}$ are each individuall H or methyl, each of $R_{r1}$ and $R_{r2}$ being the same or different.

An example of this type of compound is (cyclic structure with R groups and SO₂)

Table I includes specific examples of Lewis bases suitable for the present invention.

Preferred members of the list include aniline, pyridine, 2-picoline, 4-picoline, N,N-dimethylformamide, n-propyl alcohol because the absence of sulfur causes less contamination in the process of the present invention.

More preferably are pyridine, 2-picoline, 4-picoline because of more favorable reactivity in the presence of water.

TABLE I
BASES FOUND TO REACT WITH UO$_2$F$_2$

| Base Formula | Structure | Stoichiometry (moles base/mole UO$_2$F$_2$) |
|---|---|---|
| Pyridine | pyridine ring | 0.7–2.5 |
| 2-picoline, C$_5$H$_4$(CH$_3$)N | 2-methylpyridine | 0.67 |
| 4-picoline, C$_5$H$_4$(CH$_3$)N | 4-methylpyridine | 1.86 |
| Dimethylsulfoxide (CH$_3$)$_2$SO | H$_3$C—S(=O)—CH$_3$ | 1.0 |
| N,N-dimethylformamide HCON(CH$_3$)$_2$ | H—C(=O)—N(CH$_3$)$_2$ | 1.0 |
| Tetrahydrothiophene (CH$_2$)$_4$S | thiophene ring | 0.76 |
| Tetramethylenesulfoxide (CH$_2$)$_4$SO | sulfoxide ring | 1.5 |
| Tetramethylenesulfone (CH$_2$)$_4$SO$_2$ | sulfone ring | 1.0 |
| Methyl alcohol CH$_3$OH | CH$_3$OH | 1.16 |
| Ethyl alcohol C$_2$H$_5$OH | CH$_3$CH$_2$OH | 0.94 |
| n-propyl alcohol C$_3$H$_7$OH | CH$_3$CH$_2$CH$_2$OH | 0.95 |
| Aniline | C$_6$H$_5$NH$_2$ | 0.8 |

The combination of UO$_2$F$_2$ and the organic compound has general formulation UO$_2$F$_2$·(X)B where B is an organic Lewis base (pyridine, C$_5$H$_5$N; ethanol, C$_2$H$_5$OH; methanol, CH$_3$OH; isopropanol, iso-C$_3$H$_7$OH; etc). The value of X varies with the Lewis base involved and may have more than one value for each base.

Each of the isolated materials could be thermally decomposed to recover UO$_2$F$_2$. Invariably the decomposition was effected by heating the materials to 340° C. under oxidizing, neutral, or reducing conditions. Most of the compounds decomposed to UO$_2$F$_2$ at a temperature much lower than the 340° C. noted above.

A listing of the temperatures necessary for recovery of UO$_2$F$_2$ from compositions for several bases is given in Table II.

TABLE II
Temperatures for the Recovery of UO$_2$F$_2$

| Base (B/UO$_2$F$_2$) | T (Peak) |
|---|---|
| py (0.7) | 210° C. |
| py (1.65) | 110° C. |
| 4-picoline (1.86) | 130° C. |
| 2-picoline (0.67) | 225° C. |
| DMF (1.0) | 220° C. |
| DMSO (1.0) | 340° C. |
| THF (0.76) | 300° C. |
| THTO (1.5) | 300° C. |
| THTO$_2$ (1.0) | 130° C. |
| MeOH (1.16) | 135° C. |
| EtOH (0.94) | 90° C. |
| n-prOH (0.95) | 110° C. |

The rates of reduction of commercially available UO$_2$F$_2$ and the analogous rates for UO$_2$F$_2$ recovered from thermal decomposition of the compounds with various Lewis bases were determined at 650° C. using argon/15% H$_2$ as the reducing gas.

The results of reduction were followed using a microbalance in a thermogravimetric apparatus. Quantities of approximately 20 milligrams of the compounds were reduced at a constant temperature of 650° C. as noted above. After an initial weight loss due to the volatilization of the entrained Lewis base, the samples all lost weight due to the reduction of the resulting UO$_2$F$_2$ with H$_2$. This weight loss was monitored as a function of time until a constant weight was obtained. An average reduction rate in units of milligrams of UO$_2$F$_2$ reduced per second (mg/sec) was calculated by dividing the amount of UO$_2$F$_2$ present in each sample by the time required for reduction. The so obtained reduction rates were then normalized to that of untreated UO$_2$F$_2$ by dividing the individual reduction rates by that obtained for UO$_2$F$_2$ (untreated). As can be seen from the results in Table III, reductions were found to occur at rates greater than twice that of untreated UO$_2$F$_2$.

| | Average Reaction Rate of Reduction of the UO$_2$F$_2$ Present | |
|---|---|---|
| UO$_2$F$_2$·(X)$_B$ | mg/sec (× 10$^3$) | Normalized to UO$_2$F$_2$ |
| UO$_2$F$_2$·(1.5)H$_2$O | 3.13 | 0.7 |
| UO$_2$F$_2$ | 4.42 | 1.0 |
| UO$_2$F$_2$·(1.6)C$_5$H$_5$N | 4.90 | 1.1 |
| UO$_2$F$_2$·(0.94)C$_2$H$_5$OH | 5.81 | 1.3 |
| UO$_2$F$_2$·(1.0)C$_5$H$_5$N | 6.94 | 1.6 |
| UO$_2$F$_2$·(1.16)CH$_3$OH | 8.62 | 2.0 |
| UO$_2$F$_2$·(1.9)iso-C$_3$H$_7$OH | 9.43 | 2.1 |
| UO$_2$F$_2$·(0.75)C$_5$H$_5$N | 10.0 | 2.3 |
| UO$_2$F$_2$·(0.5)C$_5$H$_5$N | 10.2 | 2.3 |

What is claimed is:

1. A process for increasing the average reaction rate of reduction of UO$_2$F$_2$ comprising:
   (a) combining UO$_2$F$_2$ with an organic compound capable of interacting with said UO$_2$F$_2$ to form a reaction product containing from 0.5 to 3.0 moles of said organic compound per mole of UO$_2$F$_2$, said organic compound selected from the group consisting of amines of generalized formula

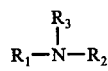

where at least one of radicals R$_1$, R$_2$ and R$_3$ is an aliphatic or an aromatic carbon network with carbon numbers of 1 to 6 with the remaining radicals, if any, being H, aliphatic heterocyclic amines of generalized formula

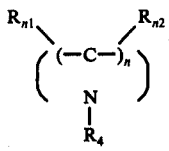

where $R_4$ is H or an aliphatic radical of carbon number of 1 to 4 and $n$ can assume values of 4 to 6 inclusive and $R_{n1}$ and $R_{n2}$ are each individually H or methyl, each of $R_{n1}$ and $R_{n2}$ being the same or different;

aromatic heterocyclic amines of generalized formula

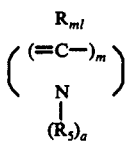

where $m$ is an integer of 4 to 6 inclusive and $a = 1$ when $m = 4$ or 6 and $a = 0$ when $m = 5$, and $R_5$ is H or aliphatic radical of carbon number 1 to 4 and $R_{m1}$ is H or methyl, aliphatic amides of formic acid of generalized formula

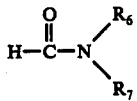

where $R_6$ and $R_7$ are each individually H or an aliphatic radical of carbon number 1 to 3, each of $R_6$ and $R_7$ being the same or different, alcohols of generalized formula $$R_8 - O - H$$

where $R_8$ is an aliphatic radical of carbon number 1 to 4 inclusive, sulfides of generalized formula $$R_9 - S - R_{10}$$

where $R_9$ and $R_{10}$ are the same or different aliphatic radicals having a carbon number of 1 to 3, aliphatic heterocyclic sulfides of generalized formula

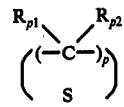

where $p$ is an integer between 4 and 6 inclusive and $R_{p1}$ and $R_{p2}$ are each individually H or methyl, each of $R_{p1}$ and $R_{p2}$ being the same or different, aliphatic heterocyclic sulfoxides of generalized formula

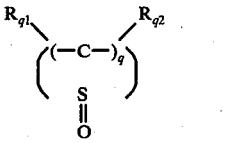

where $q$ is an integer of 4 to 6 inclusive and $R_{q1}$ and $R_{q2}$ are each individually H or methyl, each of $R_{q1}$ and $R_{q2}$ being the same or different, sulfones of generalized formula

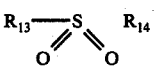

where $R_{13}$ and $R_{14}$ are aliphatic radicals of carbon number 1 to 3, aliphatic heterocyclic sulfones of generalized formula

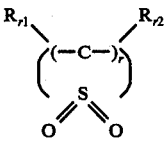

where $r$ is an integer of 4 to 6 inclusive and $R_{r1}$ and $R_{r2}$ are each individually H or methyl, each of $R_{r1}$ and $R_{r2}$ being the same or different, and mixtures thereof, (b) decomposing said reaction product to yield $UO_2F_2$ in an increased kinetically reactive state.

2. The process of claim 1 in which said organic compound is an amine.

3. The process of claim 1 in which said organic compound is an aliphatic heterocyclic amine.

4. The process of claim 1 in which said organic compound is an aromatic heterocyclic amine.

5. The process of claim 1 in which said organic compound is an aliphatic amide.

6. The process of claim 1 in which said organic compound is an alcohol.

7. The process of claim 1 in which said organic compound is a sulfide.

8. The process of claim 1 in which said organic compound is an aliphatic heterocyclic sulfide.

9. The process of claim 1 in which said organic compound is an aliphatic heterocyclic sulfoxide.

10. The process of claim 1 in which said organic compound is a sulfone.

11. The process of claim 1 in which said organic compound is an aliphatic heterocyclic sulfone.

12. The process of claim 1 in which said organic compound is selected from the group consisting of pyridine, 2-picoline, 4-picoline, N,N-dimethylformamide, tetrahydrothiophene, tetramethylenesulfoxide, tetramethylenesulfone, methyl alcohol, ethyl alcohol, n-propylalcohol, aniline, and mixtures thereof.

13. The process of claim 12 in which said organic compound is pyridine.

14. The process of claim 12 in which said organic compound is 2-picoline.

15. The process of claim 12 in which said organic compound is 4-picoline.

16. The process of claim 12 in which said organic compound is N,N-dimethylformamide.

17. The process of claim 12 in which said organic compound is tetrahydrothiophene.

18. The process of claim 12 in which said organic compound is tetramethylenesulfoxide.

19. The process of claim 12 in which said organic compound is tetramethylenesulfone.

20. The process of claim 12 in which said organic compound is methyl alcohol.

21. The process of claim 12 in which said organic compound is ethyl alcohol.

22. The process of claim 12 in which said organic compound is n-propyl alcohol.

23. The process of claim 12 in which said organic compound is aniline.

24. In a process for the production of $UO_2$ by the reduction of $UO_2F_2$, the improvement which comprises the steps of reacting said $UO_2F_2$ with an organic compound to form a reaction product containing from 0.5 to 3.0 moles of said organic compound per mole of $UO_2F_2$ and reducing said reaction product with hydrogen at an elevated temperature to yield $UO_2$, said organic compound selected from the group consisting of amines of generalized formula

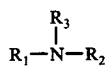

where at least one of radicals $R_1$, $R_2$ and $R_3$ is an aliphatic or an aromatic carbon network with carbon numbers of 1 to 6 with the remaining radicals, if any, being H, aliphatic heterocyclic amines of generalized formula

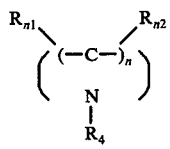

where $R_4$ is H or an aliphatic radical of carbon number of 1 to 4 and $n$ can assume values of 4 to 6 inclusive and $R_{n1}$ and $R_{n2}$ are each individually H or methyl, each of $R_{n1}$ and $R_{n2}$ being the same or different, aromatic heterocyclic amines of generalized formula

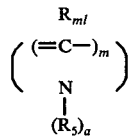

where $m$ is an integer of 4 to 6 inclusive and $a = 1$ when $m = 4$ or 6 and $a = 0$ when $m = 5$, and $R_5$ is H or aliphatic radical of carbon number 1 to 4 and $R_{m1}$ is H or methyl, aliphatic amides of formic acid of generalized formula

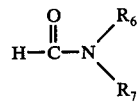

where $R_6$ and $R_7$ are each individually H or an aliphatic radical of carbon number 1 to 3, each of $R_6$ and $R_7$ being the same or different, alcohols of generalized formula

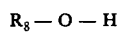

where $R_8$ is an aliphatic radical of carbon number 1 to 4 inclusive, sulfides of generalized formula

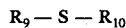

where $R_9$ and $R_{10}$ are the same or different aliphatic radicals having a carbon number of 1 to 3, aliphatic heterocyclic sulfides of generalized formula

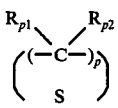

where $p$ is an integer between 4 and 6 inclusive and $R_{p1}$ and $R_{p2}$ are each individually H or methyl, each of $R_{p1}$ and $R_{p2}$ being the same or different, sulfoxides of generalized formula

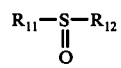

where $R_{11}$ and $R_{12}$ are aliphatic radicals of carbon number 1 to 3, aliphatic heterocyclic sulfoxides of generalized formula

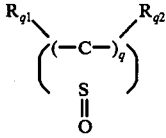

where $q$ is an integer of 4 to 6 inclusive and $R_{q1}$ and $R_{q2}$ are each individually H or methyl, each of $R_{q1}$ and $R_{q2}$ being the same or different, sulfones of generalized formula

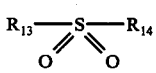

where $R_{13}$ and $R_{14}$ are aliphatic radicals of carbon number 1 to 3, aliphatic heterocyclic sulfones of generalized formula

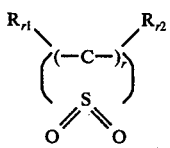

where $r$ is an integer of 4 to 6 inclusive and $R_{r1}$ and $R_{r2}$ are each individually H or methyl, each of $R_{r1}$ and $R_{r2}$ being the same or different, and mixtures thereof.

25. The process of claim 24 in which said organic compound is an amine.

26. The process of claim 24 in which said organic compound is an aliphatic heterocyclic amine.

27. The process of claim 24 in which said organic compound is an aromatic heterocyclic amine.

28. The process of claim 24 in which said organic compound is an aliphatic amide.

29. The process of claim 24 in which said organic compound is an alcohol.

30. The process of claim 24 in which said organic compound is a sulfide.

31. The process of claim 24 in which said organic comound is an aliphatic heterocyclic sulfide.

32. The process of claim 24 in which said organic compound is a sulfoxide.

33. The process of claim 24 in which said organic compound is an aliphatic heterocyclic sulfide.

34. The process of claim 24 in which said organic compound is a sulfone.

35. The process of claim 24 in which said organic compound is an aliphatic heterocyclic sulfone.

36. The process of claim 24 in which said organic compound is selected from the group consisting of pyridine, 2-picoline, 4-picoline, dimethylsulfoxide, N,N-dimethylformamide, tetrahydrothiophene, tetramethylenesulfoxide, tetramethylenesulfone, methyl alcohol, ethyl alcohol, n-propyl alcohol, aniline, and mixtures thereof.

37. The process of claim 36 in which said organic compound is pyridine.

38. The process of claim 36 in which said organic compound is 2-picoline.

39. The process of claim 36 in which said organic compound is 4-picoline.

40. The process of claim 36 in which said organic compound is dimethylsulfoxide.

41. The process of claim 36 in which said organic compound is N,N-dimethylformamide.

42. The process of claim 36 in which said organic compound is tetrahydrothiophene.

43. The process of claim 36 in which said organic compound is tetramethylenesulfoxide.

44. The process of claim 36 in which said organic compound is tetramethylenesulfone.

45. The process of claim 36 in which said organic compound is methyl alcohol.

46. The process of claim 36 in which said organic compound is ethyl alcohol.

47. The process of claim 36 in which said organic compound is n-propyl alcohol.

48. The process of claim 36 in which said organic compound is aniline.

* * * * *